United States Patent [19]

Stetter et al.

[11] Patent Number: 4,670,405
[45] Date of Patent: Jun. 2, 1987

[54] SENSOR ARRAY FOR TOXIC GAS DETECTION

[75] Inventors: Joseph R. Stetter, Naperville; Solomon Zaromb, Hinsdale; William R. Penrose, Naperville, all of Ill.

[73] Assignee: The United States of America as represented by the United States Department of Energy, Washington, D.C.

[21] Appl. No.: 585,699

[22] Filed: Mar. 2, 1984

[51] Int. Cl.⁴ .............................................. G01N 27/16
[52] U.S. Cl. ........................................ 436/151; 73/23; 422/98
[58] Field of Search ................... 73/23; 204/411, 412; 338/34; 340/634; 422/83, 93, 94, 95, 98; 436/151, 152

[56] References Cited

U.S. PATENT DOCUMENTS

| | | | |
|---|---|---|---|
| 2,149,441 | 3/1939 | Jacobson | 422/98 X |
| 2,857,251 | 10/1958 | Krogh | 422/93 |
| 3,695,848 | 10/1972 | Taguchi | 422/95 |
| 3,830,630 | 8/1974 | Kiefer et al. | 436/132 |
| 3,997,297 | 12/1976 | Jenkins et al. | 422/93 |
| 4,169,708 | 10/1979 | Muggli | 422/93 X |
| 4,225,410 | 9/1980 | Pace | 422/98 X |
| 4,315,753 | 2/1982 | Bruckenstein et al. | 422/98 X |
| 4,363,635 | 12/1982 | Hutson | 436/132 |
| 4,399,684 | 8/1983 | Advani et al. | 73/1 G |
| 4,457,161 | 7/1984 | Iwanaga et al. | 73/23 |
| 4,485,666 | 12/1984 | Higgins et al. | 73/23 |
| 4,542,640 | 9/1985 | Clifford | 422/98 X |

FOREIGN PATENT DOCUMENTS

| | | | |
|---|---|---|---|
| 915458 | 11/1972 | Canada | 73/23 |
| 58-9052 | 1/1983 | Japan | 73/23 |
| 58-11847 | 1/1983 | Japan | 73/23 |
| 885871 | 11/1981 | U.S.S.R. | 73/23 |

Primary Examiner—Barry S. Richman
Assistant Examiner—Michael S. Gzybowski
Attorney, Agent, or Firm—William Lohff; Hugh W. Glenn; Judson R. Hightower

[57] ABSTRACT

A portable instrument for use in the field in detecting and identifying a hazardous component in air or other gas including an array of small sensors which upon exposure to the gas from a pattern of electrical responses, a source of standard response patterns characteristic of various components, and microprocessor means for comparing the sensor-formed response pattern with one or more standard patterns to thereby identify the component on a display. The number of responses may be increased beyond the number of sensors by changing the operating voltage, temperature or other condition associated with one or more sensors to provide a plurality of responses from each of one or more of the sensors. In one embodiment, the instrument is capable of identifying anyone of over 50–100 hazardous components.

28 Claims, 10 Drawing Figures

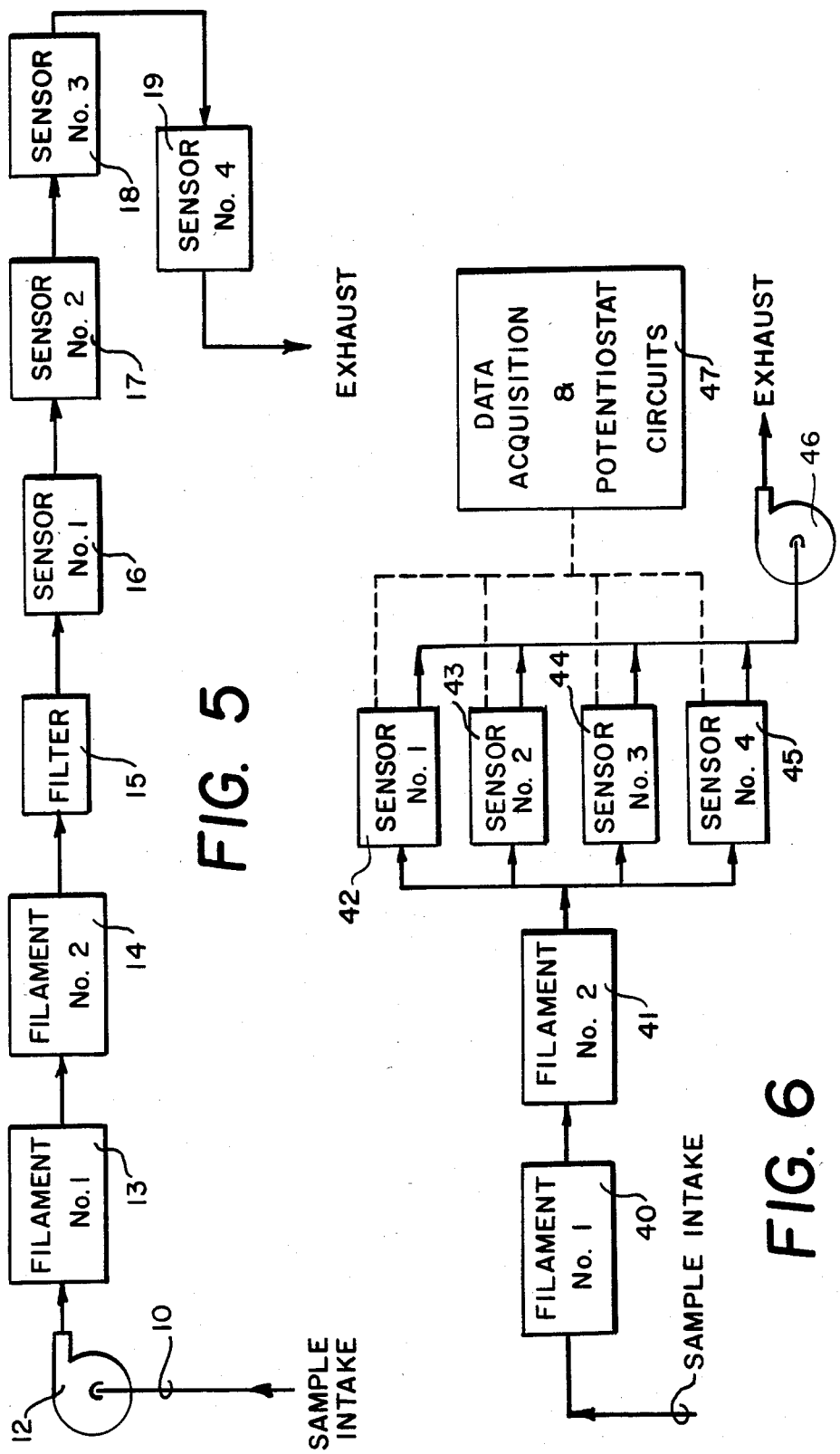

SENSOR ARRAY FOR TOXIC GAS DETECTION

CONTRACTUAL ORIGIN OF THE INVENTION

The United States Government has rights in this invention pursuant to Contract No. W-31-109-ENG-38 between the U.S. Department of Energy and the University of Chicago representing Argonne National Laboratory.

BACKGROUND OF THE INVENTION

This invention relates to analytical devices and more particularly to devices for detecting the presence of at least one pollutant or other hazardous component in a gas sample. The invention further relates to a device having a plurality of individual electrical responses from a plurality of sensors with the responses forming a pattern characteristic of a hazardous component. More specifically, the invention relates to a portable instrument capable of being used in field locations for detecting and identifying at least one hazardous component in a gas by a comparison of the pattern of responses from the sensors with one or more standard patterns stored in a memory in the instrument.

Particularly with respect to use at field locations for chemical spills and the like, devices for detecting the presence of a pollutant or other hazardous component in a gas have generally been associated with a particular selected compound. Detection devices selective for hydrogen sulfide, carbon monoxide, ammonia, and the like may be considered as representative. Essentially, these devices measure one or a few selected pollutants and are not designed to identify the pollutant. When a gas for analysis may contain an unknown pollutant, it is usually necessary to obtain a sample of the gas and send it to a laboratory for a remote analysis. The time required for the transmittal of the sample and its analysis usually delays a meaningful identification of any harmful components and/or their concentration in the gas for a significant time.

Semi-portable versions of the more powerful laboratory gas chromatographic or infrared analyzers have been commercially introduced in recent years. Besides being rather heavy, bulky, unwieldy, and expensive, these instruments have certain inherent limitations. The gas chromatographic devices cannot operate in a continuous real-time monitoring mode. The infrared analyzers require a delicate optical system with a rather long absorption path, which contributes to their bulk, weight, and unwieldiness. These instruments must usually be operated and their results interpreted only by well-trained professionals.

One object of this invention is a device for detecting and identifying one or more hazardous components of a gas. A second object of this invention is a device capable of identifying a hazardous component in a gas from the response pattern of a plurality of sensors. A third object of the invention is a device for identifying any of a number of unknown hazardous components in a gas. Another object of the invention is a device capable of providing a varied pattern of responses and thereby capable of identifying a plurality of possible hazardous components in a gas. An additional object of the invention is a device capable of on-site analysis of a gas. A further object of the invention is a portable device capable of being easily transported to field locations and of being operated and used by unskilled or semi-skilled personnel. These and other objects will become apparent from the Detailed Description.

SUMMARY OF THE INVENTION

Briefly, the invention relates to an analytical device for identifying at least one hazardous component in a gas such as air through the use of an array of small, preferably tiny sensors such as existing electrochemical, semiconductor, heated noble metal catalyst, or photoionization sensors, it has been found that the pattern of responses from these sensors provides identification of the component when compared to a standard response pattern which may be established for the component in the memory of the device. In the device, at least two of the sensors produce different electrical responses from the chemical interaction of the component or its derivative with each sensor. The array preferably also includes at least one heating filament capable of producing one or more derivatives by oxidation or pyrolysis of the component. In addition, the responses from the sensors may be varied by changes in one or more of the operational conditions such as voltage, temperature, sample flow rate, or diversion of the sample flow through a selective chemical filter, and the like, so that the number of different responses is greater than the number of sensors and the number of components in the gas. This increase in the number of different responses improves the selectivity of the device with respect to the identification of the hazardous components.

The device is particularly useful as a small portable instrument suitable for use in the field for identifying one or more hazardous components from a chemical spill or other emergency condition. Programming means are provided to form a response pattern from the array of sensors and compare the formed response pattern with one or more standard response patterns stored in a memory in the instrument. In one embodiment, the device includes two different heating filaments and four different electrochemical sensors with programming means capable of changing at least one operating condition for the four electrochemical sensors to identify any one of over 50–100 hazardous components. In addition, analysis of the responses also provides data on the concentration levels of the hazardous component or components. All these functions are self-contained in the instrument and are preprogrammed so that they may be carried out by generally unskilled personnel. In general, the instrument has a power requirement below about 2 watts and the sensors are arranged in a space less than about 8 cm by 15 cm by 8 cm.

The device further has the capability of continuously monitoring levels of a hazardous substance and triggering an alarm when a predetermined level is reached.

BRIEF DESCRIPTION OF THE DRAWINGS

FIG. 5 is a block diagram of one embodiment of the invention with a sensor array having sample chambers connected in series.

FIG. 6 is a block diagram of a second embodiment of the invention with a sensor array having sample chambers connected in parallel.

DETAILED DESCRIPTION OF THE PREFERRED EMBODIMENT

Figure 1A:
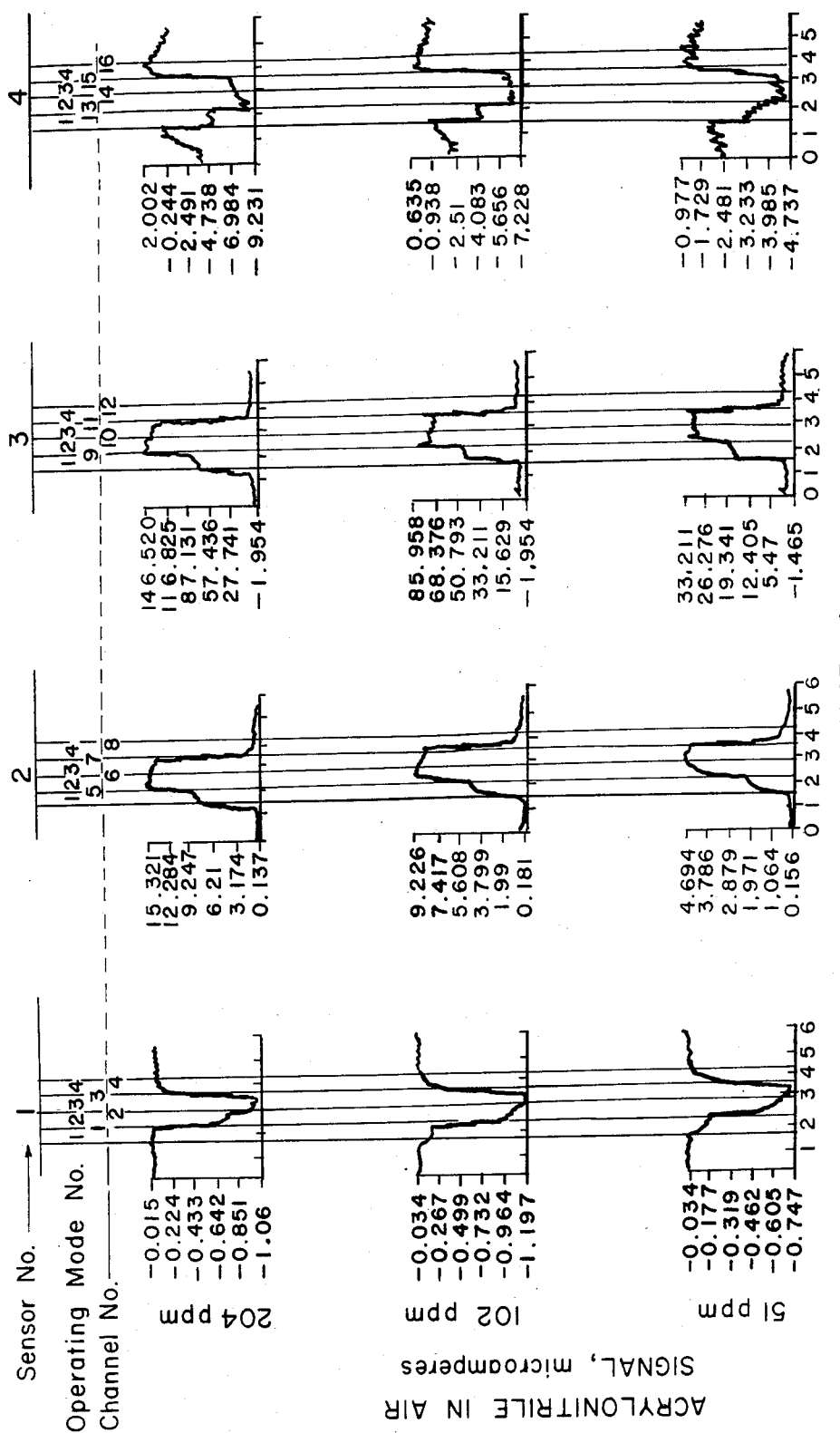
FIGS. 1A and 1B are a series of graphs showing the response patterns for acrylonitrile from an array of sensors including four electrochemical sensors.

The invention is directed to a method and the associated device for identifying at least one hazardous component in a gas. The invention is particularly important for use in the field as a portable instrument for detecting one or more hazardous components in air from a chemical spill, fire, or other form of pollution. Representative hazardous components with which the invention provides useful results include acrylonitrile, ammonia, benzene, carbon monoxide, carbon tetrachloride, chlorine, chloroform, cyclohexane, ethyl acrylate, formaldehyde, hydrogen sulfide, nitric oxide, nitrogen dioxide, nitromethane, pyridine, sulfur dioxide, sulfuryl fluoride, tetrahydrofuran, toluene, and vinyl acetate.

The TWA (time-weighted average) toxic levels of the above hazardous components vary from about 1 ppm (parts per million) for chlorine or formaldehyde to about 300 ppm for cyclohexane. However, for short term exposure, it may be more important to detect and identify one or more of these components at levels in the order of about 2 to 400 (usually 10 to 50) ppm. In the invention, these components are detected by their chemical interaction or that of their derivatives with the sensors in the array. Usually, the component has a chemically active group or groups or may be oxidized or reduced to form one or more derivatives having an active group or groups such as carbon monoxide, nitrogen dioxide, etc.

In the invention, each of the sensors in an array is provided with a housing or other gas containment system forming a sample chamber with the combination forming a sensing means. Means are provided for introducing a gas sample to the sensing means which typically may be the sensing electrode of an electrochemical, especially of an amperometric, gas sensor. The sensors include at least two and preferably at least 3-4 sensors having different electrical responses to a component or its derivative to provide a plurality of different responses. Usually, the responses differ between sensors for the same component and between the same sensor for different components.

As an illustration of the operation of an instrument embodying the invention, the instrument can be set to perform one of two principal functions—monitoring or identification. When monitoring for the presence of any unknown air contaminant, the sensor array is connected directly to a sampling probe, and a signal from any of the sensors indicates the presence of a possibly hazardous component near the probe intake. To identify the detected component, a sample is first drawn from the probe intake into a 1-liter (L) sampling bag. The collected sample is then drawn through the sensor array at a rate of about 0.01–0.1 L per minute, and the sensors are switched into four differently selective modes at appropriate intervals (usually 40 seconds/interval). The responses of each sensor at the end of each interval are recorded in one of 16 independent data channels, and the relative magnitudes of these response signals provide the information needed to identify the particular component giving rise to the observed signals. The microprocessor-controller identifies a compound based on the recorded data and then sets the sensor array for maximum sensitivity to that compound in the monitoring mode. The number of sensors and time required may be varied according to the complexity of the analyte. Simpler mixtures may require smaller arrays and fewer modes of operation than the more complex analytes. It can also set the alarm to correspond to an appropriate level associated with the short term exposure limit (STEL) or immediate danger to life and health (IDLH) concentration of the identified compound.

The sensor array may comprise electrochemical, catalytic or semiconductor-type sensors, or combinations of these and other types of portable low-power gas sensors, and preferably will be primarily electrochemical. The sensor array may also include one or more heating filaments having exposed catalytic surfaces. Suitable types of electrochemical sensors include amperometric sensors having gold or platinum sensing electrodes supported on either an ion-exchange, e.g., polyfluorosulfonic acid, membrane, which also serves as the sensor electrolyte, or on a gas-permeable electrolyte-impermeable porous polytetrafluoroethylene membrane, with the sensor electrolyte being either a strong acid, such as $H_2SO_4$ or $H_3PO_4$, or a strong base, such as KOH, in aqueous solution. Sensors using other metal and non-metal electrodes in aqueous or non-aqueous solutions may also be used. The array may also include one or more heating filaments containing catalytic material, such as platinum, palladium, iridium, rhodium or gold, and preferably two separate filaments, e.g., one of platinum and one of rhodium. These filaments may function to provide different degrees of oxidation of the component and also to act as sensors whose electrical current will vary with the concentration of the component.

When a gas sample is caused to flow past the filaments before being exposed to a sensor array, as indicated in either of FIGS. 5 or 6, then the partial oxidation or pyrolysis of a component caused by heating one of the filaments becomes equivalent to converting the sensor array to a differently selective operating mode.

An alternative or complementary way of increasing the number of differently selective operating modes, and thereby achieving improved selectivity, is to divert the sample past one or more selective chemical filters (e.g., cartridges containing materials having strong chemical affinity for certain compounds) by means of electronically controlled solenoid valves (not shown). Such filters may comprise activated charcoal or other adsorbents to remove organic vapors or chemical reagents such as triethanolamine on a support to remove nitrogen dioxide. By comparing the responses of the sensor array to a sample passed through no chemical filter with the responses to the same sample passed through one or more different chemical filters, identification of the tested compound or compounds may be greatly facilitated.

In any case, for a number 5 of differently selective sensors in an array and a number M of differently selective operating modes, the maximum number of independent parameters (or data channels) P that can be obtained upon exposure to a test sample is given by the product MS, i.e., $P=MS$. The larger the value of P, the larger the number of different components that can be identified by a sensor array.

Figure 1B:
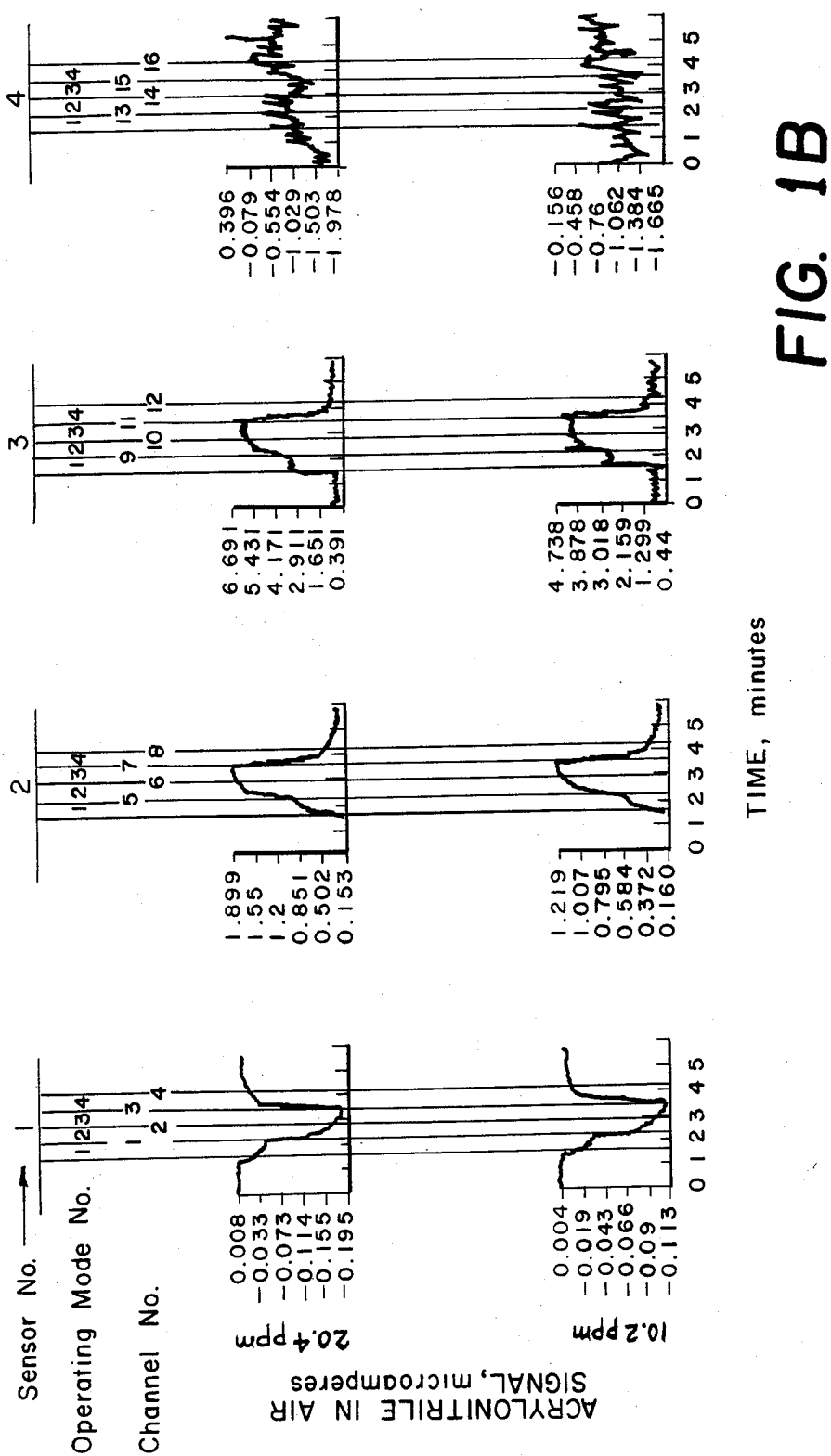
Figure 2:
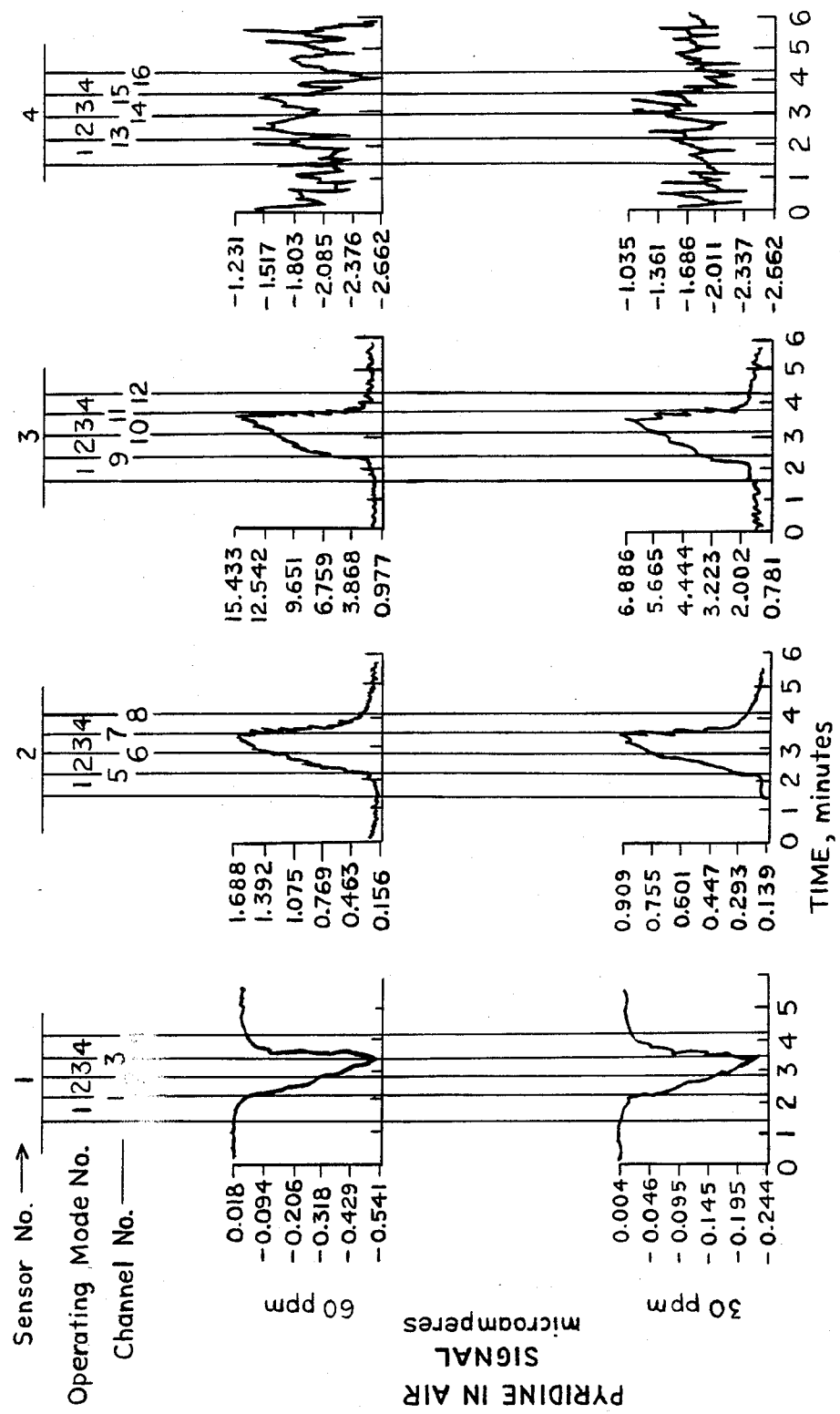
FIG. 2 is a series of graphs showing the response patterns to pyridine from an array of sensors including four electrochemical sensors.
Figure 3:
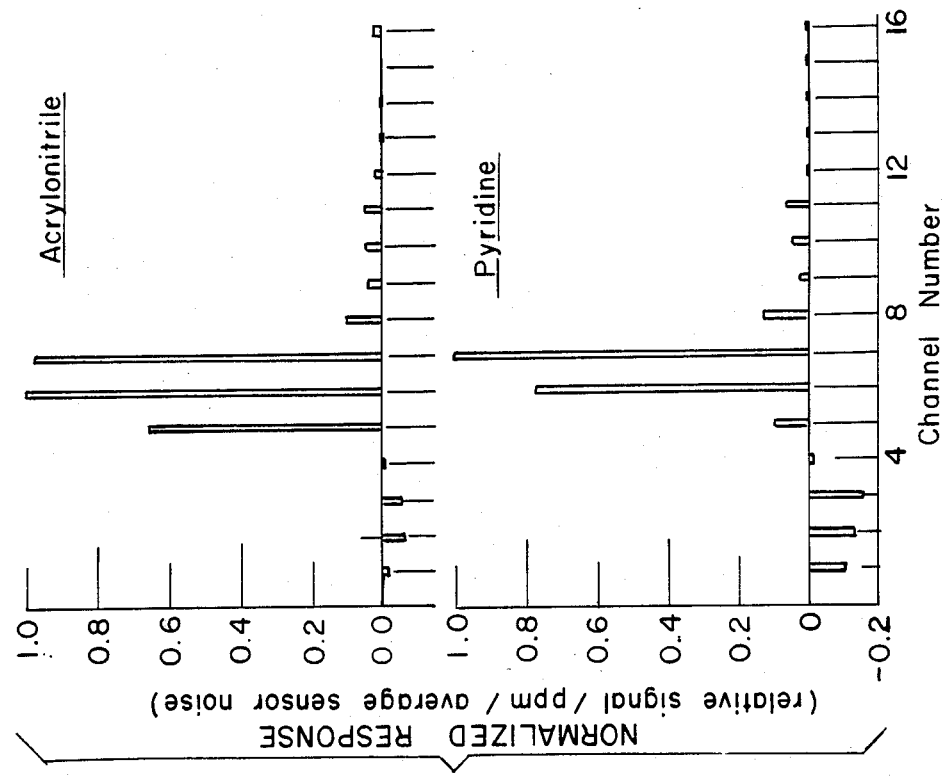
FIG. 3 is a pair of histograms of normalized responses of channels to toxic vapors of acrylonitrile and pyridine.

As an illustration of the detection of hazardous components, FIGS. 1 and 2 provide data for acrylonitrile and pyridine, respectively. The array includes four different electrochemical toxic gas sensors—two with pure gold mesh sensing electrodes embedded in a polyfluorosulfonic acid ion-exchange membrane, one of the electrodes being kept at a potential 1.0 volt and one at a potential of 1.4 volt versus RHE (the reversible hydrogen electrode), one with a similar electrode made of platinized platinum mesh and kept at 1.3 volt versus RHE and one with a sensing electrode of platinum black bonded to a porous tetrafluoroethylene membrane, immersed in an approximately 25-30 wt. % sulfuric acid electrolyte, and potentiostated at 1.1 volt versus RHE—and two heated noble metal filaments—one of platinum and one of rhodium—that function to oxidize or partially oxidize many compounds in air. The four sensors may be rapidly switched to one of the following four operating modes: (a) platinum filament heated to about 850° C.; (b) rhodium filament heated to about 900° C.: (c) rhodium filament heated to about 1000° C.; and (d) both filaments off. In this arrangement, four modes and four sensors provide a total of 16 independent data channels as illustrated in FIGS. 1 and 3. In FIG. 1, each of four sensors was exposed to predetermined amounts of acrylonitrile in air and was operating in each of the foregoing four modes As indicated by the data, each sensor has a different electrical response pattern to exposure to acrylonitrile with the response changing with concentration. A similar result is shown in FIG. 2 for pyridine. The responses in FIGS. 1 and 2, when normalized as set forth in FIG. 3, exhibit different histogram patterns for different compounds, thereby permitting identification of a sampled compound. Moreover, as illustrated in FIG. 4, the magnitude or amplitude of the strongest channels in FIG. 3 may be used as an indication of the concentration of the identified hazardous component.

Figure 4:
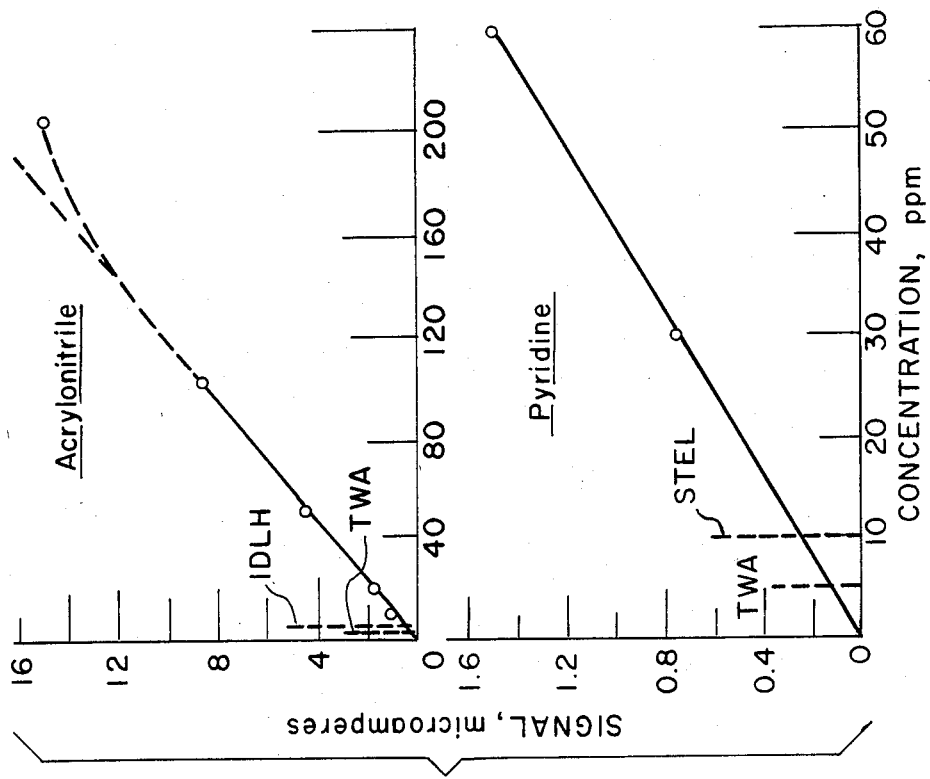
FIG. 4 is a pair of graphs showing the proportionality of the response signals in the strongest channels of FIG. 3 to the sampled toxic vapor concentration.

Further with respect to FIG. 4, the data also show the time-weighed average threshold exposure level (TWA) and the STEL or IDLH concentrations of the two components.

The device may function either to monitor the level of a component or to identify unknown components. FIG. 3 shows that channel 6 provides the strongest signal for acrylonitrile while channel 7 provides the strongest signal for pyridine. Therefore, the sensor array as a monitor will be tuned to channel 6 after having identified acrylonitrile or to channel 7 after having identified pyridine.

Programming means are provided to form sensor responses into a response pattern. As illustrated in FIG. 3, the responses may be positive, at or about zero, or negative. These responses collectively form one or more response patterns which serve to identify the component.

Advantageously, the programming means include means for comparing the formed response pattern with one or more standard or previously established patterns each being characteristic of a particular component or type of component. Preferably, the programming means also include a memory which provides the standard patterns for the comparison.

Prior to the comparison, the initial or first response pattern is converted to a second pattern in which noise and blank readings are removed. As an illustration, the responses in FIG. 3 are obtained by dividing the responses initially obtained by the corresponding toxic gas concentration and also by the average noise of each sensor corresponding to a given channel. The values in each channel are then normalized by dividing them by the highest response in the 16-channel response pattern to provide FIG. 3.

In environments where the number of possible detectable components exceeds the number P of independent parameters or data channels, gas samples containing mixtures of more than one unknown detectable component may be resolved. To resolve such a mixture of unknown components in a gas sample, the programming means can first reject those candidate compounds whose response patterns call for significant signals in those channels in which the tested sample gave no significant response. In the examples of FIGS. 1-3, an insignificant response in Channel No. 1 (corresponding to Sensor No. 1 in Operating Mode No. 1) would exclude pyridine as a candidate compound, but would be compatible with the presence of acrylonitrile. This can be followed by additional prescreening steps. For instance programming means can then select those remaining candidate compounds whose response patterns exhibit strong responses in the same channels as in the actually observed response pattern. For instance, strong responses in Channel Nos. 5, 6 and 7 of FIG. 3, would point to acrylonitrile as a possible candidate compound. Finally, should this selection process yield more than one likely candidate compound, then the concentrations of each of these likely candidates may be estimated by solving several simultaneous algebraic equations (developed from an analysis of the standard response pattern) based on a comparison of the actual response pattern with the response patterns of the likely candidate compounds. All of these comparisons can be performed rapidly using a microprocessor built into the instrument.

FIG. 5 and 6 provide schematic sketches of sensor array arrangements. As illustrated in FIG. 5, the sample inlet 10 includes pump 12 to cause a flow of sample to filaments 13 and 14 which may be individually switched on or off or both on and off during the analysis. Filter 15 is provided to remove particulates. The resulting sample may be the initial component or its derivative or derivatives depending on whether filaments 13 and/or 14 are utilized. The resulting sample is then fed sequentially to sensors 16, 17, 18 and 19. These sensors are also arranged so that the first few sensors in the sequence interact with only minimal amounts of the sample without significantly altering the concentration introduced into the sample chambers of the subsequent sensors.

In FIG. 6, the sample is fed to filaments 40 and 41 and then to sensors 42, 43, 44 and 45 arranged in parallel. After interacting with these sensors, the sample is removed via pump 46. Data acquisition and potentiostat circuits 47 are provided to receive the responses and provide changes in the voltages of the sensors.

Figure 7A:
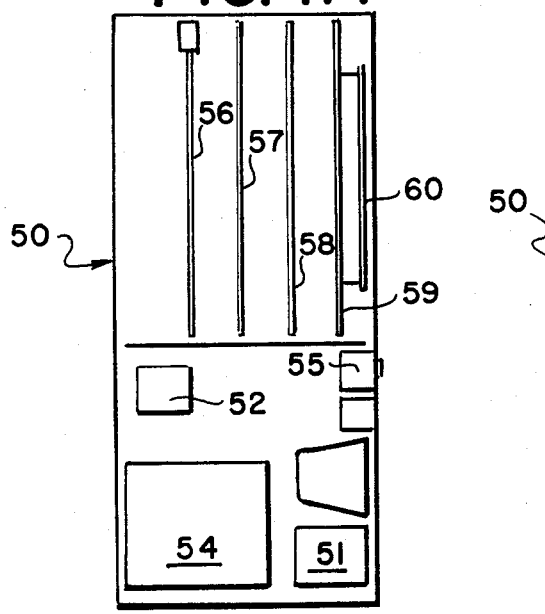
FIG. 7A represents a side view of a portable instrument embodying the invention.
Figure 7B:
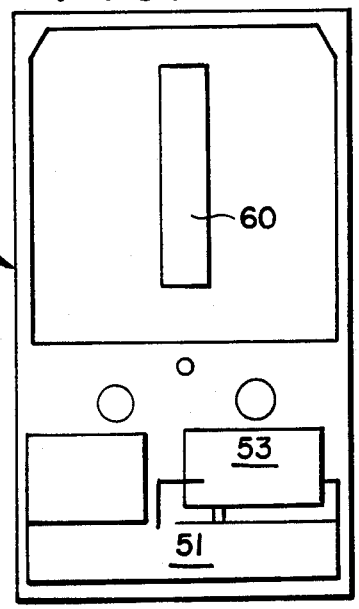
FIG. 7B represents a front view of the portable instrument of FIG. 7A.

FIGS. 7A and 7B provides an arrangement of side and front views of a portable instrument. As illustrated, a housing 50 is provided which may be about 8 cm. by 28 cm. by 22 cm. Electrochemical cells 51 and filament 52 are provided as the array. Pump 53 acts to introduce the sample. Batteries 54 provide portable power. Filter 55 acts to remove particles. Four circuit boards are provided. Board 56 provides the CPU (central processing unit), board 57 provides the potentiometer and self-test circuits, board 58 provides the analog circuit, and board 59 provides power, alarm and display circuits. Display module 60 provides a display of data from each test.

Figure 8:
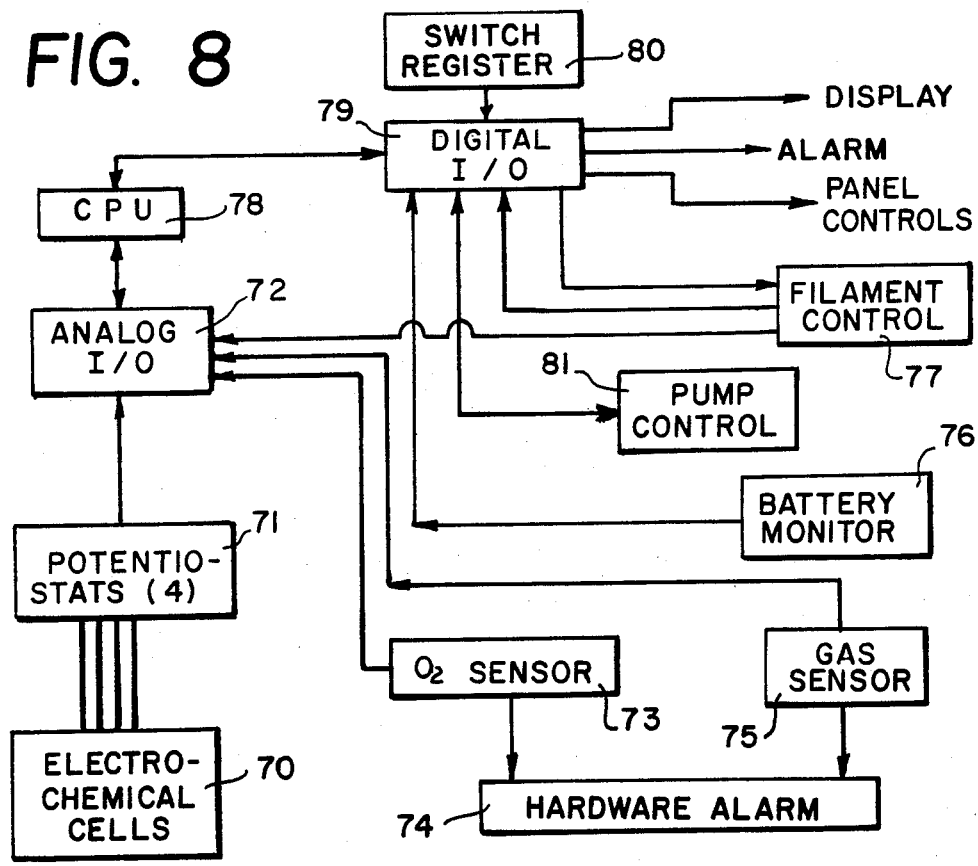
FIG. 8 is a block diagram of the data generating and processing systems associated with the invention.

FIG. 8 illustrates the interconnection of the parts of the device. Electrochemical cells 70 are controlled by potentiostats 71 with the responses from cells 70 being fed to an analog input/output 72 which also receives data and/or instructions from oxygen sensor 73, alarm 74, flammable gas sensor 75, filament control 77, and CPU 78. Digital input-out 79 also is operated by switch register 80, battery monitor 76 filament control 77, CPU 78, and pump control 81. Display and alarm signals are provided by digital input/output 79.

The device is provided with microprocessor programming means in which a master program is used to select any of a plurality of functional programs which in turn may utilize one or more of certain of the other functional programs and one or more utility programs. Selection of the functional program in the preferred embodiment is by the use of an appropriate key on the face of the housing. A display is provided to show the name of the component identified by the programming means in the test or the component being monitored.

In one preferred embodiment, the functional programs are named the Ident mode, the Select mode, the Universal mode, the Zero mode, the Calibrate mode, and the Test mode. All of these programs are operated using key strokes by the individual operators that activate the microprocessor to run the desired program. As illustrations of these modes, the following description is provided with the term "gas" intended to refer to the "component" being detected.

The Ident mode collects a set of data from an unknown gas (16 data points, 4 electrochemical cells in 4 modes), subtracts a set of zero data (the signals obtained from background air), multiplies by calibration data (obtained from a calibration gas to take into account the changing performance of cells, if any), and by treating the result as a 16-coordinate vector, compares the data to a series of pattern data sets stored in a library for various gases (the unknown gas data is normalized, and a euclidean distance calculation is performed between it and every pattern set). The gas having the pattern data which is the closest to the unknown is selected as the proper identification for the gas, and any pattern data sets having a distance from the unknown equal to or less than twice the mininum distance are selected as possible or incipient identifications. The concentration of the gas is calculated by multiplying the data from the strongest channel by a concentration coefficient stored in the pattern data library, and from the results of this calculation the percent IDLH level is also determined. All of this information is displayed, and alarms are set otf at the and 25% and 100% IDLH level (a beeping buzzer and flashing LEDs (light-emitting diodes) at 25% or greater, and a steady buzzer and LEDs at 100% and higher). Finally, the option is provided to the operator to review the information (gas identified, concentration, percent IDLH, number of incipient misidentifications, and a list of incipient misidentifications) or to exit back to master program or a routine "Main" by pressing the proper key. Exiting back to Main shuts off any alarms.

The Select mode allows the operator to choose which of the gases in the pattern library to monitor. The gas is chosen by advancing forwards or backwards through the library, using the keyboard (only the name of the gas is displayed). When the proper gas is located, the operator can choose to either initiate the mode or exit back to MAIN. Once initiated, the device is operated only in the most sensitive mode, so that only four channels of data are taken. The euclidean distance is calculated based on only four channels to give a measure of how well the measured gas fits the pattern vector. This feature is intended to warn of mixtures of vapors or of mislabeling of chemicals. Select mode provides a measurement in a time appropriate for the mode (32 to 50 sec). The program may be interrupted after any cycle.

The Universal mode is to detect possibly hazardous compounds prior to their identification. A Pt or Rh filament cycles on and off with 5–20-second duty cycles. The sensor responses are reported to the operator as a set of four arbitrary numbers; the alarm is triggered when any cell output exceeds a predetermined threshold.

The no-signal state of the device must be frequently measured. Upon entering the Zero mode, the 16 channels of information are acquired using the same routine (Volts) that is called by the Ident mode. Afterward, the 16-element vector is transferred to a special register. In subsequent measurements, this value is subtracted from all incoming data in the Ident, Select, or Universal modes.

Similarly, the aging of electrochemical cells and filaments is expected to cause gradual changes in responses over time. The Calibrate mode is designed to calculate a correction factor for each channel. A sample of a calibration gas such as sulfur dioxide is attached to the device. The data acquisition subroutine (Volts) is called. The resulting vector is compared to that stored in the pattern library, and the ratio is stored in a special register. Each subsequent measurement in the Ident or Select modes is corrected by this ratio. If Calib is not selected, a default vector is loaded into the calibrate register, representing the state of the cells at the time the library was compiled.

The Test mode gives access to the same monitor program that was used in program development on the device. The monitor program permits these functions.
 (a) Reading any portion of memory.
 (b) Changing values in RAM memory.
 (c) Resetting the instrument.
 (d) Calling certain subroutines used for device testing. For example, Control can be used to manually control pump speed and both filaments.

Test mode is not intended for routine operator use. If Test mode is inadvertently entered, two keystrokes will escape this mode.

As covered by the above disclosure, the invention provides an analytical device useful in the field for performing the three functions of detecting, identifying and measuring a component in a gas. Advantageously, the device is portable and includes microprocessor programming means by which multiple functions may be carried out with respect to a gas component and the results depicted on a display on the device.

The foregoing description of embodiments of the invention has been presented for purposes of illustration and description. It is not intended to be exhaustive or to limit the invention to the precise form disclosed, and obviously many modifications and variations are possible in light of the above teaching.

The embodiments of the invention in which an exclusive property or privilege is claimed are defined as follows:

1. A method for identifying at least one component in a gas sample, comprising the steps of:

introducing a gas sample suspected of containing at least one component to an array of sensors for exposure of said component or a derivative thereof to said sensors, said array including plural sensors having differing electrical responses to said at least one component of said derivative thereof dependent on the chemical interaction of said at least one component or said derivative thereof with each of said sensors and also dependent on an operational condition of at least one of said plurality of sensors;

changing said operational condition during the exposure of said sensors to the gas sample to provide a plurality of different responses from said at least one sensor, forming a response pattern from the responses of said sensors, and comparing the formed response pattern with a set of previously established response patterns to identify said at least one component.

2. The method of claim 1 wherein the step of forming the response pattern includes the step of converting a first response pattern to a second response pattern.

3. The method of claim 1 wherein the step of comparing includes comparing the formed response pattern with a plurality of previously established response patterns, and further includes the step of first eliminating at least one of said plurality of previously established response patterns by comparing an insignificant response of said at least one sensor for one condition with said at least one previously established response pattern having a significant response for said at least one sensor for the same operational condition.

4. The method of claim 1, wherein the changing of the operational condition is carried out to provide a plurality of responses greater in number than the number of said sensors and not smaller than the number of components to be identified in said gas.

5. The method of claim 1 wherein the step of forming said response pattern results in at least one response pattern identifiable with a concentration of said at least one component and said step of comparing response patterns provides a comparison of said at least one response pattern with a previously established response pattern for determining said concentration.

6. The method of claim 1 including the step of providing a portable device including said array of sensors and wherein the formation and comparison of the response pattern are carried out with the device in the field.

7. The method of claim 1, wherein the total number of components that can be detected is greater than the product of the number of sensors times the number of different operational conditions.

8. An instrument for indeifying at least one hazardous component in a gas sample, comprising sensing means including an array of sensors, means for introducing to said sensing means a gas sample suspected of containing at least one hazardous component, said array including plural sensors having differing electrical responses to said at least one component or a derivative thereof dependent on the chemical interaction of asid at least one component or a derivative thereof with each of said sensors and also dependent on an operational condition of at least one of said plurality of sensors, means for changing said operational condition during the exposure of said sensors to the gas sample to provide a plurality of different responses from said at least one sensor, means for forming a response pattern from said sensing means upon exposure to said sample, means for providing a plurality of previously established response patterns including a previously established response pattern for identifying said at least one component, and means for comparing the formed response pattern with at least one previously established response pattern to identify said at least one component.

9. The instrument of claim 8 wherein said array includes a heating filament in addition to said sensors, said heating filament being capable of forming a derivative of said at least one component.

10. The instrument of claim 8 wherein said array includes four sensors, each of said four sensors having electrical responses differing from those of the others of said four sensors.

11. The instrument of claim 8 having means for providing electrical power of up to about 2 watts.

12. The instrument of claim 8 wherein said sensing means includes two different heating filaments and four different electrochemical sensors.

13. The instrument of claim 8 wherein said forming means includes means for converting a first response pattern to a second response pattern prior to the comparison of patterns.

14. The instrument of claim 8 wherein said comparing means incudes means for comparing an insignificant response of said at least one sensor for one operational condition with a previously established response pattern having a significant response for said at least one sensor for the same operational condition.

15. The instrument of claim 8 wherein said changing means comprises means for diverting said sample past a chemically selective filter.

16. The instrument of claim 8 including programming means for selectively identifying an unknown component or monitoring the concentration of a known component of the gas.

17. The instrument of claim 16 wherein said programming means includes means for mathematically modifying the responses for sensor calibration and background noise.

18. The instrument of claim 8 including a carrying case including electrical power means, said array of sensors, said means for forming said response pattern, memory means for storing said previously established response patterns, and said comparison means.

19. The instrument of claim 18, wherein said power means includes at least one electrical battery.

20. The instrument of claim 8 wherein said changing means enables said at least one sensor to provide more than one response.

21. The instrument of claim 20 wherein said sensors include at least one semiconductor sensor.

22. The instrument of claim 20 wherein said changing means comprises at least one heating filament disposed upstream from said array of sensors.

23. The instrument of claim 22 wherein said array is arranged with the sensors having the higher responses downstream from the other sensors.

24. The instrument of claim 20 wherein said changing means enables each of a plurality of said sensors to provide more than one response with the number responses for said array of sensors being greater than the number of said sensors.

25. The instrument of claim 24 wherein said array of sensors is arranged in a space less than about 8 cm by 15 cm by 8 cm.

26. The instrument of claim 24 wherein said sensors include a plurality of electrochemical sensors.

27. An instrument for identifying and estimating the concentrations of a plurality of components in a gas sample, comprising:

sensing means including an array of differently selective sensors, means for introducing to said sensing means a gas sample suspected of containing one or more components of a predetermined number of components that are detectable by said array, the number of said sensors being greater than one and fewer than said predetermined number of components, means for forming a multi-channel response pattern from said sensing means upon exposure to said sample, means fo comparing said formed pattern with a set of previously established patterns, said comparing means including means for eliminating those of said previously established response patterns which call for significant signals in those channels in which said formed pattern has no significant signal, and means for processing the remaining ones of said previously established response patterns so as to identify and estimate the concentration of each of said one or more components in said sample.

28. The instrument of claim 27, and further including means for changing an operational condition of said array to provide a plurality of different responses from each of said sensors, said predetermined number of components being greater than the product of the number of sensors times the number of different operational conditions.

* * * * *